(12) United States Patent
Axten et al.

(10) Patent No.: US 7,232,832 B2
(45) Date of Patent: Jun. 19, 2007

(54) ANTIBACTERIAL AGENTS

(75) Inventors: Jeffrey Michael Axten, Collegeville, PA (US); William Henry Miller, Collegeville, PA (US); Mark Andrew Seefeld, Collegeville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 32 days.

(21) Appl. No.: 10/533,502

(22) PCT Filed: Nov. 4, 2003

(86) PCT No.: PCT/US03/35201

§ 371 (c)(1),
(2), (4) Date: May 2, 2005

(87) PCT Pub. No.: WO04/096982

PCT Pub. Date: Apr. 11, 2003

(65) Prior Publication Data

US 2006/0166977 A1   Jul. 27, 2006

Related U.S. Application Data

(60) Provisional application No. 60/423,858, filed on Nov. 5, 2002.

(51) Int. Cl.
*C07D 401/06*   (2006.01)
*A61K 31/47*   (2006.01)

(52) U.S. Cl. ............... 514/300; 514/314; 546/113; 546/152

(58) Field of Classification Search .......... 546/113, 546/152; 514/300, 314
See application file for complete search history.

(56) References Cited

U.S. PATENT DOCUMENTS

| | | | |
|---|---|---|---|
| 6,194,413 B1 | 2/2001 | Bhatnagar et al. | 514/252.11 |
| 6,403,610 B1 | 6/2002 | Malleron et al. | 514/314 |
| 6,602,882 B1 | 8/2003 | Davies et al. | 514/300 |
| 6,602,884 B2 | 8/2003 | Bacque et al. | 514/314 |
| 6,603,005 B2 | 8/2003 | Baque et al. | 546/176 |
| 6,803,369 B1 | 10/2004 | Erskine et al. | 514/253.06 |
| 6,815,547 B2 | 11/2004 | Bacque et al. | 546/174 |
| 6,841,562 B2 | 1/2005 | Bacque et al. | 514/314 |
| 6,903,217 B2 | 6/2005 | Bacque et al. | 546/180 |
| 6,911,442 B1 | 6/2005 | Davies et al. | 514/230.5 |
| 6,962,917 B2 | 11/2005 | Davies et al. | 514/264.1 |
| 6,989,447 B2 | 1/2006 | Markwell et al. | 546/152 |
| 7,001,913 B1 | 2/2006 | Davies et al. | 514/300 |
| 2003/0203917 A1 | 10/2003 | Erskine et al. | 514/253.06 |
| 2003/0212084 A1 | 11/2003 | Hatton et al. | 514/266.22 |
| 2004/0053928 A1 | 3/2004 | Davies et al. | 514/248 |
| 2004/0077655 A1 | 4/2004 | Dartois et al. | 514/253.05 |
| 2004/0077656 A1 | 4/2004 | Markwell et al. | 514/253.05 |
| 2004/0087619 A1 | 5/2004 | Bacque et al. | 514/314 |
| 2004/0138219 A1 | 7/2004 | Davies et al. | 514/243 |
| 2004/0171620 A1 | 9/2004 | Brooks et al. | 514/248 |
| 2004/0198755 A1 | 10/2004 | Dartois et al. | 514/266.22 |
| 2004/0198756 A1 | 10/2004 | Davies et al. | 514/266.22 |
| 2004/0224946 A1 | 11/2004 | Bigot et al. | 514/227.8 |
| 2005/0032800 A1 | 2/2005 | Bigot et al. | 514/243 |
| 2005/0085494 A1 | 4/2005 | Daines et al. | 514/266.22 |
| 2005/0159411 A1 | 7/2005 | Daines et al. | 514/224.8 |
| 2006/0014749 A1 | 1/2006 | Davies et al. | 514/249 |
| 2006/0040925 A1 | 2/2006 | Davies et al. | 514/222.8 |
| 2006/0041123 A1 | 2/2006 | Axten et al. | 544/48 |
| 2006/0058287 A1 | 3/2006 | Axten et al. | 514/224.2 |
| 2006/0079546 A1 | 4/2006 | Davies et al. | 514/300 |
| 2006/0116512 A1 | 6/2006 | Axten et al. | 540/553 |
| 2006/0189601 A1 | 8/2006 | Hennessy et al. | 514/222.8 |
| 2006/0189604 A1 | 8/2006 | Axten et al. | 514/224.2 |

FOREIGN PATENT DOCUMENTS

| | | |
|---|---|---|
| CA | 2500320 A1 | 4/2004 |
| EP | 1218370 B1 | 12/2004 |
| WO | WO97/17973 | 5/1997 |
| WO | WO 99/37635 | 7/1999 |
| WO | WO00/21948 A1 | 4/2000 |
| WO | WO 00/21952 | 4/2000 |
| WO | WO 00/43383 | 7/2000 |
| WO | WO 00/78748 A1 | 12/2000 |
| WO | WO 01/07432 A2 | 2/2001 |
| WO | WO 01/07433 A2 | 2/2001 |
| WO | WO 01/25227 A2 | 4/2001 |
| WO | WO 02/08224 A1 | 1/2002 |
| WO | WO 02/24684 A1 | 3/2002 |
| WO | WO 02/40474 A2 | 5/2002 |
| WO | WO 02/50040 A1 | 6/2002 |
| WO | WO 02/50061 A1 | 6/2002 |

(Continued)

OTHER PUBLICATIONS

U.S. Appl. No. 09/889820, filed Sep. 20, 2001, Davies et al., Quinoline Derivatives as Antibacterials.

(Continued)

*Primary Examiner*—Zinna N. Davis
(74) *Attorney, Agent, or Firm*—Loretta J. Sauermelch; Mary E. McCarthy; Charles M. Kinzig

(57) ABSTRACT

Quinoline and naphthyridine derivatives useful in the treatment of bacterial infections in mammals, particularly humans.

11 Claims, No Drawings

FOREIGN PATENT DOCUMENTS

| | | |
|---|---|---|
| WO | WO 02/056882 A1 | 7/2002 |
| WO | WO 02/072572 A1 | 9/2002 |
| WO | WO 02/096907 A1 | 12/2002 |
| WO | WO 03/010138 A2 | 2/2003 |
| WO | WO 03/064421 A1 | 8/2003 |
| WO | WO 03/064431 A2 | 8/2003 |
| WO | WO 03/087098 A1 | 10/2003 |
| WO | WO 2004/002490 A2 | 1/2004 |
| WO | WO 2004/002992 A1 | 1/2004 |
| WO | WO 2004/014361 A1 | 2/2004 |
| WO | WO 2004/024712 A1 | 3/2004 |
| WO | WO 2004/024713 A1 | 3/2004 |
| WO | WO 2004/035569 A2 | 4/2004 |
| WO | WO 2004/041210 A2 | 5/2004 |
| WO | WO 2004/050036 A2 | 6/2004 |
| WO | WO 2004/058144 A2 | 7/2004 |
| WO | WO 2004/087145 A2 | 10/2004 |
| WO | WO 2004/087647 | 10/2004 |
| WO | WO 2004/089947 A2 | 10/2004 |
| WO | WO2005/016916 | 2/2005 |

OTHER PUBLICATIONS

U.S. Appl. No. 10/868351, filed Jun. 15, 2004, Erskine et al., Compounds and Methods for the Treatment of Disease.

U.S. Appl. No. 10/199933, filed Jul. 19, 2002, Erskine et al., Compounds and Methods for the Treatment of Disease.

U.S. Appl. No. 10/937468, filed Sep. 9, 2004, Erskine et al., Compounds and Methods for the Treatment of Disease.

U.S. Appl. No. 10/533501, filed Dec. 3, 2003, Axten et al., Antibacterial Agents.

ANTIBACTERIAL AGENTS

This application claims the benefit of U.S. Provisional Application Ser. No. 60/423,585, filed Nov. 5, 2002.

FIELD OF THE INVENTION

This invention relates to novel compounds, compositions containing them and their use as antibacterials.

BACKGROUND OF THE INVENTION

The emergence of pathogens resistant to known antibiotic therapy is becoming a serious global healthcare problem (Chu, et al., (1996) *J. Med. Chem.*, 39: 3853–3874). Thus, there is a need to discover new broad-spectrum antibiotics useful in combating multidrug-resistant organisms. Importantly, it has now been discovered that certain compounds have antibacterial activity, and, therefore, may be useful for the treatment of bacterial infections in mammals, particularly in humans.

WO99/37635, WO00/21948, WO00/21952, WO0043383, WO00/78748, WO01/07433, WO01/07432, WO01/25227, WO0208224, WO0224684, PCT/GB01/05653, PCT/GB01/05661 and WO02040474 disclose quinoline and naphthyridine derivatives having antibacterial activity.

SUMMARY OF THE INVENTION

This invention comprises compounds of the formula (I), as described hereinafter, which are useful in the treatment of bacterial infections. This invention is also a pharmaceutical composition comprising a compound according to formula (I) and a pharmaceutically acceptable carrier. This invention is also a method of treating bacterial infections in mammals, particularly in humans.

DETAILED DESCRIPTION OF THE INVENTION

This invention provides a compound of formula (I) or a pharmaceutically acceptable derivative thereof:

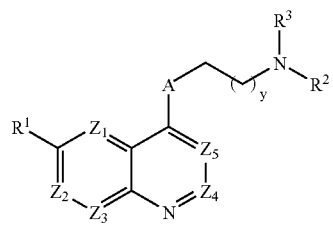

(I)

wherein:
one of $Z_1$, $Z_2$, $Z_3$, $Z_4$ and $Z_5$ is N, one is $CR^{1a}$ and the remainder are CH, or one or two of $Z_1$, $Z_2$, $Z_3$, $Z_4$ and $Z_5$ are independently $CR^{1a}$ and the remainder are CH;

$R^1$ and $R^{1a}$ are independently hydrogen; hydroxy; $(C_{1-6})$alkoxy unsubstituted or substituted by $(C_{1-6})$alkoxy, amino, piperidyl, guanidino or amidino any of which is optionally N-substituted by one or two $(C_{1-6})$alkyl, acyl or $(C_{1-6})$alkylsulphonyl groups, $CONH_2$, hydroxy, $(C_{1-6})$ alkylthio, heterocyclylthio, heterocyclyloxy, arylthio, aryloxy, acylthio, acyloxy or $(C_{1-6})$alkylsulfonyloxy; $(C_{1-6})$ alkoxy-substituted $(C_{1-6})$alkyl; halogen; $(C_{1-6})$alkyl; $(C_{1-6})$alkylthio; trifluoromethyl; trifluoromethoxy; nitro; cyano; azido; acyl; acyloxy; acylthio; $(C_{1-6})$alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups;

provided that when $Z_1$, $Z_2$, $Z_3$, $Z_4$ and $Z_5$ are $CR^{1a}$ or CH, then $R^1$ is not hydrogen;

A is a substituted or unsubstituted 5 membered aromatic heterocyclic ring of formula (C):

(C)

wherein:
$W_1$ and $W_2$ are each independently selected from N, O, S, and $CR^8$;
$W_3$ is N or C;
$W_4$ is N, O, S, or $CR^8$;
each $R^8$ is independently selected from hydrogen; hydroxy; halogen; trifluoromethyl; trifluoromethoxy; cyano; nitro; azido; acyl; acyloxy; acylthio; amino, mono- and di-$(C_{1-6})$alkylamino; and substituted and unsubstituted $(C_{1-6})$alkoxy, $(C_{1-6})$alkyl, $(C_{3-7})$cycloalkyl, aminocarbonyl, $(C_{1-6})$alkylthio, $(C_{1-6})$alkylsulphonyl, and $(C_{1-6})$alkylsulphoxide;

$R^2$ is hydrogen, or $(C_{1-6})$alkyl or $(C_{2-6})$alkenyl optionally substituted with 1 to 3 groups selected from:
amino optionally substituted by one or two $(C_{1-4})$alkyl groups; carboxy; $(C_{1-4})$alkoxycarbonyl; $(C_{1-4})$alkylcarbonyl; $(C_{2-4})$alkenyloxycarbonyl; $(C_{2-4})$alkenylcarbonyl; aminocarbonyl wherein the amino group is optionally substituted by hydroxy, $(C_{1-4})$alkyl, hydroxy$(C_{1-4})$alkyl, aminocarbonyl $(C_{1-4})$alkyl, $(C_{2-4})$alkenyl, $(C_{1-4})$alkylsulphonyl, trifluoromethylsulphonyl, $(C_{2-4})$alkenylsulphonyl, $(C_{1-4})$alkoxycarbonyl, $(C_{1-4})$alkylcarbonyl, $(C_{2-4})$ alkenyloxycarbonyl or $(C_{2-4})$alkenylcarbonyl; cyano; tetrazolyl; 3-hydroxy-3-cyclobutene-1,2-dione-4-yl; 2,4-thiazolidinedione-5-yl; tetrazol-5-ylaminocarbonyl; 5-oxo-1,2,4-oxadiazol-3-yl; halogen; $(C_{1-4})$alkylthio; trifluoromethyl; hydroxy optionally substituted by $(C_{1-4})$ alkyl, $(C_{2-4})$alkenyl, $(C_{1-4})$alkoxycarbonyl, $(C_{1-4})$alkylcarbonyl, $(C_{2-4})$alkenyloxycarbonyl, $(C_{2-4})$ alkenylcarbonyl; oxo; $(C_{1-4})$alkylsulphonyl; $(C_{2-4})$ alkenylsulphonyl; or $(C_{1-4})$aminosulphonyl wherein the amino group is optionally substituted by $(C_{1-4})$alkyl or $(C_{2-4})$alkenyl;

$R^3$ is a group —U—$R^4$ where
U is selected from $CH_2$, C=O, and $SO_2$ and
$R^4$ is a substituted or unsubstituted bicyclic carbocyclic or heterocyclic ring system (A):

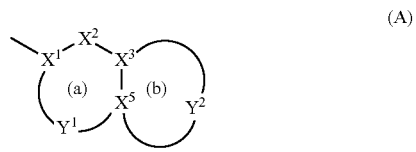

(A)

containing up to four heteroatoms in each ring in which ring (a) is aromatic and ring (b) is aromatic or non-aromatic;

$X^1$ is C;

$X^2$ is N or $CR^5$;

$X^3$ and $X^5$ are C;

$Y^1$ is a 1 to 2 atom linker group, each atom of which is independently selected from N and $CR^5$;

$Y^2$ is a 2 to 6 atom linker group, each atom of $Y^2$ being independently selected from N, $NR^7$, O, S(O)x, CO, $CR^5$ and $CR^5R^6$;

each of $R^5$ and $R^6$ is independently selected from: hydrogen; $(C_{1-4})$alkylthio; halo; carboxy$(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy$(C_{1-4})$alkyl; mercapto $C_{1-4})$alkyl; $(C_{1-4})$alkoxy; nitro; cyano; carboxy; amino or wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl; or $(C_{2-6})$alkenyl; $(C_{1-4})$alkylsulphonyl; $(C_{2-4})$alkenylsulphonyl; or aminosulphonyl wherein the amino group is optionally mono- or di-substituted by $(C_{1-4})$alkyl or $(C_{2-4})$alkenyl; aryl; aryl$(C_{1-4})$alkyl; or aryl$(C_{1-4})$alkoxy;

each $R^7$ is independently hydrogen; trifluoromethyl; $(C_{1-4})$alkyl unsubstituted or substituted by hydroxy, $(C_{1-6})$alkoxy, $(C_{1-6})$alkylthio, halo or trifluoromethyl; $(C_{2-4})$alkenyl; aryl; aryl $(C_{1-4})$alkyl; arylcarbonyl; heteroarylcarbonyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl; and x is 0, 1, or 2;

y is 1, or 2; or a pharmaceutically acceptable salt thereof.

Also included in this invention are pharmaceutically acceptable addition salts, complexes or prodrugs of the compounds of this invention. Prodrugs are considered to be any covalently bonded carriers which release the active parent drug according to formula (I) in vivo.

The invention also provides a pharmaceutical composition, in particular for use in the treatment of bacterial infections in mammals, particularly humans, comprising a compound of formula (I), or a pharmaceutically acceptable derivative thereof, and a pharmaceutically acceptable carrier.

The invention further provides a method of treatment of bacterial infections in mammals, particularly in humans, which method comprises the administration to a mammal in need of such treatment an effective amount of a compound of formula (I), or a pharmaceutically acceptable derivative thereof.

Preferably $Z_5$ is CH or N, $Z_3$ is CH or CF and $Z_1$, $Z_2$ and $Z_4$ are each CH, or $Z_1$ is N, $Z_3$ is CH or CF and $Z_2$, $Z_4$ and $Z_5$ are each CH.

When $R^1$ or $R^{1a}$ is substituted alkoxy it is preferably $(C_{2-6})$alkoxy substitituted by optionally N-substituted amino, guanidino or amidino, or $(C_{1-6})$alkoxy substituted by piperidyl. Suitable examples of $R^1$ and $R^{1a}$ alkoxy include methoxy, trifluoromethoxy, n-propyloxy, iso-butyloxy, aminoethyloxy, aminopropyloxy, aminobutyloxy, aminopentyloxy, guanidinopropyloxy, piperidin-4-ylmethyloxy, phthalimido pentyloxy or 2-aminocarbonylprop-2-oxy.

Preferably $R^1$ and $R^{1a}$ are independently methoxy, amino $(C_{3-5})$alkyloxy, guanidino$(C_{3-5})$alkyloxy, piperidyl$(C_{3-5})$alkyloxy, nitro or halo. More preferably $R^1$ and $R^{1a}$ are independently methoxy, amino$(C_{3-5})$alkyloxy or guanidino $(C_{3-5})$alkyloxy. Most preferably $R^1$ is methoxy and $R^{1a}$ is H or when $Z_3$ is $CR^{1a}$ it may be C—F.

When $Z_5$ is $CR^{1a}$, $R^{1a}$ is preferably hydrogen, cyano, hydroxymethyl or carboxy, most preferably hydrogen.

Examples of ring (C) are substituted and unsubstituted pyrrole, isopyrrole, pyrazole, imidazole, triazole, tetrazole, oxazole, isoxazole, furan, thiophene, thiazole, isothiazole, and oxadiazole. Preferably ring (C) is substituted or unsubstituted pyrrole, thiophene, furan, thiazole, or triazole. Most preferably ring (C) is triazole or thiazole Preferably $R^8$ is hydrogen or $(C_{1-6})$alkyl.

$R^2$ is preferably hydrogen; $(C_{1-6})$alkyl substituted with carboxy, optionally substituted hydroxy, optionally substituted aminocarbonyl, optionally substituted amino or $(C_{1-6})$ alkoxycarbonyl; or $(C_{2-6})$alkenyl substituted with $(C_{1-6})$ alkoxycarbonyl or carboxy. More preferred groups for $R^2$ are hydrogen, carboxymethyl, hydroxyethyl, aminocarbonylmethyl, ethoxycarbonylmethyl, ethoxycarbonylallyl and carboxyallyl. Most preferred $R^2$ group is hydrogen.

Preferably in the heterocyclic ring (A) $Y^2$ has 3–5 atoms, more preferably 4 atoms, including $NR^7$, O or S bonded to $X^5$ and NHCO bonded via N to $X^3$, or O or NH bonded to $X^3$. Ring (a) is preferably substituted and unsubstituted phenyl and pyridine. Preferably ring (b) is substituted and unsubstituted pyridine, dioxane, piperidine, morpholin-3-one, thiomorpholin-3-one, oxazolidin-2-one, thiadiazole, and thiazepan-5-one. Examples of ring (A) groups include substituted or unsubstituted: 1,1,3trioxo-1,2,3,4-tetrahydro1 ⁶-benzo[1,4]thiazin-3-one-6-yl, benzo[1,3]dioxol-5-yl, 4H-benzo[1,4]oxazin-3-one-6-yl, 2,3-dihydro-benzo[1,4]dioxin-6-yl, 2-oxo-2,3-dihydro-benzooxazol-6-yl, 3-substituted-3H-benzooxazol-2-one-6-yl, 3-substituted-3H-benzooxazole-2-thione-6-yl, 3-substituted-3H-benzothiazol-2-one-6-yl, 4H-benzo[1,4]oxazin-3-one-6-yl (3-oxo-3,4-dihydro-2H-benzo[1,4]oxazin-6-yl), 4H-benzo[1,4]thiazin-3-one-6-yl (3-oxo-3,4-dihydro-2H-benzo[1,4] thiazin-6-yl), 4H-benzo[1,4]oxazin-3-one-7-yl, 4-oxo-2,3,4, 5-tetrahydro-benzo[b][1,4]thiazepine-7-yl, 5-oxo-2,3-dihydro-5H-thiazolo[3,2-a]pyrimidin-6-yl, benzo[1,3] dioxol-5-yl, 1H-pyrido[2,3-b][1,4]thiazin-2-one-7-yl (2-oxo-2,3-dihydro-1H-pyrido[2,3-b]thiazin-7-yl), 2,3-dihydro-1H-pyrido[2,3-b][1,4]thiazin-7-yl, 2-oxo-2,3-dihydro-1H-pyrido[3,4-b]thiazin-7-yl, 2,3-dihydro-[1,4]dioxino [2,3-b]pyridin-6-yl, 2,3-dihydro-[1,4]dioxino[2,3-c]pyridin-7-yl, 2,3-dihydro-[1,4]dioxino[2,3-b]pyridin-7-yl, 3,4-dihydro-2H-benzo[1,4]oxazin-6-yl, 3,4-dihydro-2H-benzo [1,4]thiazin-6-yl, 3-oxo-3,4-dihydro-2H-pyrido[3,2-b][1,4] oxazin-6-yl, 3,4-dihydro-2H-pyrido[3,2-b][1,4]thiazin-6-yl, 3-oxo-3,4-dihydro-2H-pyrido[3,2-b][1,4]thiazin-6-yl, 3,4-dihydro-1H-quinolin-2-one-7-yl, 3,4-dihydro-1H-quinoxalin-2-one-7-yl, 6,7-dihydro-4H-pyrazolo[1,5-a]pyrimidin-5-one-2-yl, 5,6,7,8-tetrahydro-[1,8]naphthyridin-2-yl, 2-oxo-3,4-dihydro-1H-[1,8]naphthyridin-6-yl, 4H-pyrido[3,2-b][1, 4]thiazin-3-one-6-yl, 4H-pyrido[3,2-b][1,4]oxazin-3-one-6-yl, 1,2,3,4-tetrahydro-[1,8]naphthyridine-7-yl, 1H-pyrido[3, 2-b][1,4]thiazin-2-one-7-yl, and 6-fluoro-2,3-dihydrobenzo [1,4]dioxine-7-yl.

$R^5$ and $R^6$ are preferably independently selected from hydrogen, halo, hydroxy, $(C_{1-4})$alkoxy, trifluoromethoxy, nitro, cyano, aryl$(C_{1-4})$alkoxy and $(C_{1-4})$alkylsulphonyl. More preferably $R^5$ and $R^6$ are both hydrogen More preferably each $R^5$ is selected from hydrogen, chloro, fluoro, hydroxy, methoxy, trifluoromethoxy, benzyloxy, nitro, cyano and methylsulphonyl. Most preferably $R^6$ is selected from hydrogen, fluorine or nitro.

$R^7$ is preferably H if in ring (a) or in addition $(C_{1-4})$alkyl such as methyl or isopropyl when in ring (b). More preferably, in ring (b) $R^7$ is H when $NR^7$ is bonded to $X^3$ and $(C_{1-4})$alkyl when $NR^7$ is bonded to $X^5$.

Most Preferred Examples of $R^4$ Are:
4H-benzo[1,4]thiazin-3-one-6-yl,
4H-pyrido[3,2-b][1,4]thiazin-3-one-6-yl,
4H-pyrido[3,2-b][1,4]oxazin-3-one-6-yl,
1,2,3,4-tetrahydro-[1,8]naphthyridine-7-yl,
1H-pyrido[3,2-b][1,4]thiazin-2-one-7-yl,
4H-benzo[1,4]oxazin-3-one-6-yl, and
6-fluoro-2,3-dihydrobenzo[1,4]dioxine-7-yl.

Preferred Compounds of this Invention Are:
3-Oxo-3,4-dihydro-2H-benzo[1,4]thiazine-6-sulfonic acid {3-[4-(6-methoxy-[1,5]naphthyridin-4-yl)-[1,2,3]triazol-1-yl]-propyl}amide and 6-{[(2-{4-[6-(methoxy)-1,5-naphthyridin-4-yl]-1,3-thiazol-2-yl)ethyl)amino]methyl}-2H-pyrido[3,2-b][1,4]thiazin-3(4H)-one dihydrochloride; or a pharmaceutically acceptable salt thereof.

Unless otherwise defined, the term $(C_{1-6})$alkyl when used alone or when forming part of other groups (such as the 'alkoxy' group) includes substituted or unsubstituted, straight or branched chain alkyl groups containing 1 to 6 carbon atoms. Examples of $(C_{1-6})$alkyl include methyl, ethyl, n-propyl, isopropyl, n-butyl, isobutyl and tert-butyl groups.

The term $(C_{2-6})$alkenyl means a substituted or unsubstituted alkyl group of 2 to 6 carbon atoms, wherein one carbon-carbon single bond is replaced by a carbon-carbon double bond. Examples of $(C_{2-6})$alkenyl include ethylene, 1-propene, 2-propene, 1-butene, 2-butene, isobutene and the several isomeric pentenes and hexenes. Both cis and trans isomers are included.

The term $(C_{3-7})$cycloalkyl refers to substituted or unsubstituted carbocyclic system of three to seven carbon atoms, which may contain up to two unsaturated carbon-carbon bonds. Examples of $(C_{3-7})$cycloalkyl include cyclopropyl, cyclobutyl, cyclopentyl, cyclopentenyl, cyclohexyl, cyclohexenyl, and cycloheptyl.

Unless otherwise defined, suitable substituents for any $(C_{1-6})$alkyl, $(C_{2-6})$alkenyl, and $(C_{3-7})$cycloalkyl groups includes up to three substituents selected from the group consisting of hydroxy, halogen, nitro, cyano, carboxy, amino, amidino, sulphonamido, unsubstituted $(C_{1-6})$alkoxy, trifluromethyl, acyloxy, quanidino, unsubstituted $(C_{3-7})$cycloalkyl, aryl, and heterocyclic.

Halo or halogen includes fluoro, chloro, bromo and iodo.
Haloalkyl moieties include 1–3 halogen atoms.

Unless otherwise defined, the term "heterocyclic" as used herein includes optionally substituted aromatic and non-aromatic, single and fused, rings suitably containing up to four hetero-atoms in each ring selected from oxygen, nitrogen and sulphur, which rings may be unsubstituted or C-substituted by, for example, up to three groups selected from $(C_{1-4})$alkylthio; halo; carboxy$(C_{1-4})$alkyl; halo $(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy $(C_{1-4})$alkyl; mercapto$(C_{1-4})$alkyl; $(C_{14})$alkoxy; nitro; cyano, carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; optionally substituted aryl, aryl$(C_{1-4})$alkyl or aryl$(C_{1-4})$alkoxy and oxo groups.

Each heterocyclic ring suitably has from 4 to 7, preferably 5 or 6, ring atoms. A fused heterocyclic ring system may include carbocyclic rings and need include only one heterocyclic ring.

Compounds within the invention containing a heterocyclyl group may occur in two or more tautometric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include H; trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; aryl; aryl $(C_{1-4})$alkyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl.

When used herein the term "aryl", includes optionally substituted phenyl and naphthyl.

Aryl groups may be optionally substituted with up to five, preferably up to three, groups selected from $(C_{1-4})$alkylthio; halo; carboxy$(C_{1-4})$alkyl; halo $(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy $(C_{1-4})$alkyl; mercapto$(C_{1-4})$alkyl; $(C_{14})$alkoxy; nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; phenyl, phenyl$(C_{1-4})$alkyl or phenyl$(C_{1-4})$alkoxy The term "acyl" includes formyl and $(C_{1-6})$alkylcarbonyl group.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Since the compounds of formula (I) are intended for use in pharmaceutical compositions it will readily be understood that they are each provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (1) or pharmaceutically acceptable derivative thereof.

Pharmaceutically acceptable derivatives of the above-mentioned compounds of formula (I) include the free base form or their acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. Compounds of formula (I) may also be prepared as the N-oxide. Compounds of formula (I) having a free carboxy group may also be prepared as an in vivo hydrolysable ester. The invention extends to all such derivatives.

Examples of suitable pharmaceutically acceptable in vivo hydrolysable ester-forming groups include those forming esters which break down readily in the human body to leave the parent acid or its salt. Suitable groups of this type include those of part formulae (i), (ii), (iii), (iv) and (v):

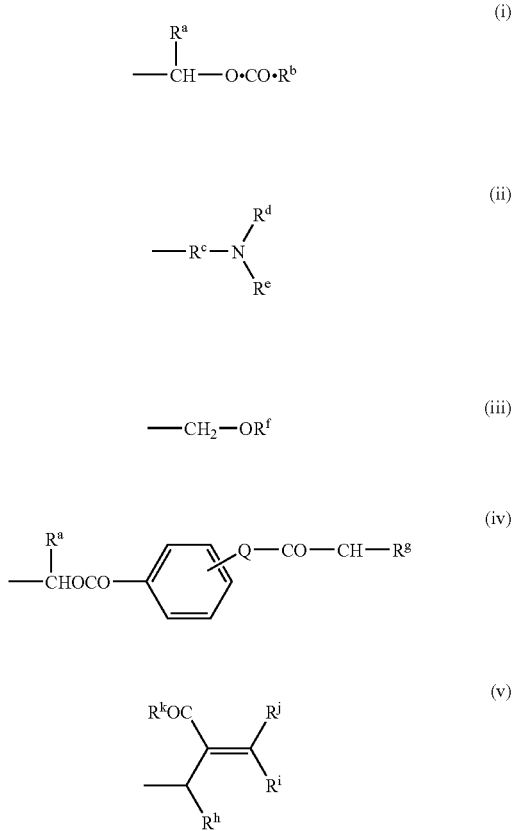

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$ alkoxy, phenyl, benzyl, $(C_{3-7})$ cycloalkyl, $(C_{3-7})$ cycloalkyloxy, $(C_{1-6})$ alkyl $(C_{3-7})$ cycloalkyl, 1-amino $(C_{1-6})$ alkyl, or 1-$(C_{1-6}$ alkyl) amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$ alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy $(C_{1-6})$ alkoxy or aryl.

Examples of suitable in vivo hydrolysable ester groups include, for example, acyloxy($C_{1-6}$)alkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; $(C_{1-6})$alkoxycarbonyloxy($C_{1-6}$)alkyl groups, such as ethoxycarbonyloxymethyl, α-ethoxycarbonyloxyethyl and propoxycarbonyloxyethyl; di($C_{1-6}$)alkylamino($C_{1-6}$)alkyl especially di($C_{1-4}$)alkylamino($C_{1-4}$)alkyl groups such as dimethylaminomethyl, dimethylaminoethyl, diethylaminomethyl or diethylaminoethyl; 2-((($C_{1-6}$)alkoxycarbonyl)-2-($C_{2-6}$)alkenyl groups such as 2-(isobutoxycarbonyl)pent-2-enyl and 2-(ethoxycarbonyl)but-2-enyl; lactone groups such as phthalidyl and dimethoxyphthalidyl.

A further suitable pharmaceutically acceptable in vivo hydrolysable ester-forming group is that of the formula:

wherein $R^k$ is hydrogen, $(C_{1-6})$alkyl or phenyl.

Certain of the above-mentioned compounds of formula (I) may exist in the form of optical isomers, e.g. diastereoisomers and mixtures of isomers in all ratios, e.g. racemic mixtures. The invention includes all such forms, in particular the pure isomeric forms. For examples the invention includes compound in which an A-B group CH(OH)—CH$_2$ is in either isomeric configuration the R-isomer is preferred. The different isomeric forms may be separated or resolved one from the other by conventional methods, or any given isomer may be obtained by conventional synthetic methods or by stereospecific or asymmetric syntheses.

Certain reagents are abbreviated herein. DCC refers to dicyclohexylcarbodiimide, DMAP refers to dimethylaminopyridine, DIEA refers to diisopropylethyl amine, EDC refers to 1-(3-dimethylaminopropyl)-3-ethylcarbodiimide, hydrochloride. HOBt refers to 1-hydroxybenzotriazole, THF refers to tetrahydrofuran, DIEA refers to diisopropylethylamine, DEAD refers to diethyl azodicarboxylate, PPh$_3$ refers to triphenylphosphine, DIAD refers to diisopropyl azodicarboxylate, DME refers to dimethoxyethane, DMF refers to dimethylformamide, NBS refers to N-bromosuccinimide, Pd/C refers to a palladium on carbon catalyst, PPA refers to polyphosphoric acid, DPPA refers to diphenylphosphoryl azide, BOP refers to benzotriazol-1-yloxy-tris(dimethyl-amino)phosphonium hexafluorophosphate, HF refers to hydrofluoric acid, TEA refers to triethylamine, TFA refers to trifluoroacetic acid, PCC refers to pyridinium chlorochromate.

The compounds of the present invention were prepared by the methods illustrated in Schemes I and II.

Scheme 1

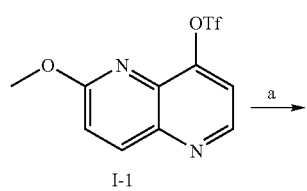
I-1 a ↓

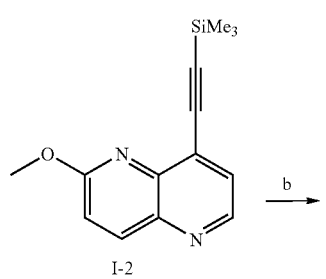
I-2 b ↓

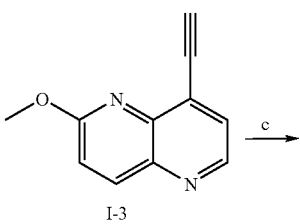
I-3 c ↓

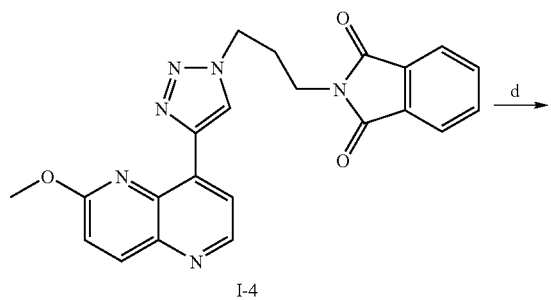
I-4 d ↓

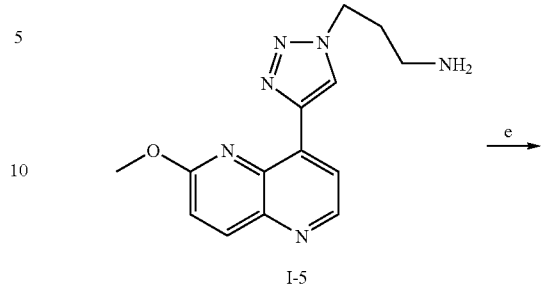
I-5 e ↓

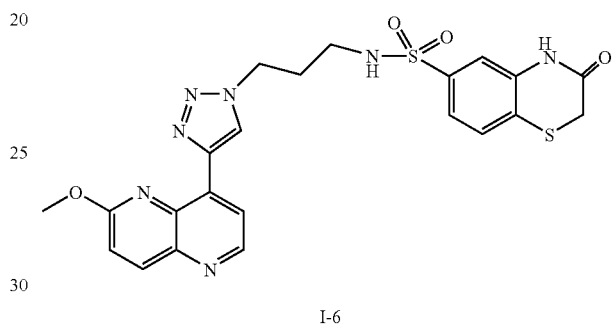
I-6

Reagents and conditions:
(a) Trimethylsilylacetylene, CuI, PdCl₂(PPh₃)₂, Et₃N, CH₂Cl₂; (b) K₂CO₃, CH₃OH; (c) 2-(3-azidopropy) isoindole-1,3-dione, toluene; (d) N₂H₄·H₂O, EtOH; (e) 3-oxo-3,4-dihydro-2H-benzo[1,4]thiazine-6-sulfonyl chloride, CHCl₃, Et₃N.

Triflate (I-1) is reacted under Sonogashira coupling conditions (Sonogashira, K.; Tohda, Y; Hagihara, N. Tetrahedron Left. 1975, pp. 4467–4470) with an aromatic halide or aromatic triflate to afford I-2. Removal of the trimethylsilyl protecting group is carried out under basic conditions to give the alkyne I-3. The use of protecting groups to mask reactive functionality is well-known to those of skill in the art, and other protecting groups are listed in standard reference volumes, such as Greene, "Protective Groups in Organic Synthesis" (published by Wiley-Interscience). The terminal alkyne derivative is then reacted with an azide under thermal cyclization conditions to yield the triazole I-4. Removal of the phthalamide protecting group is accomplished using hydrazine or other suitable reagents as described in Greene, referenced above, to afford the free amine I-5. The amine is then reacted with a suitable electrophile such as an arylsulfonyl chloride to form the sulfonamide I-6. For example, 3-oxo-3,4-dihydro-2H-benzo[1,4]thiazine-6-sulfonyl chloride is converted to a sulfonamide by reaction with an amine in aprotic solvents such as DMF, CH₂Cl₂, CH₃CN and using an added base, such as triethylamine (Et₃N), diisopropylethylamine ((i-Pr)₂NEt), or K₂CO₃ to scavenge for acid formed in situ. Many additional methods for sulfonamide formations are known, and can be found in standard reference books, such as "Compendium of Organic Synthetic Methods", Vol. I–VI (published by Wiley-Interscience).

Scheme II

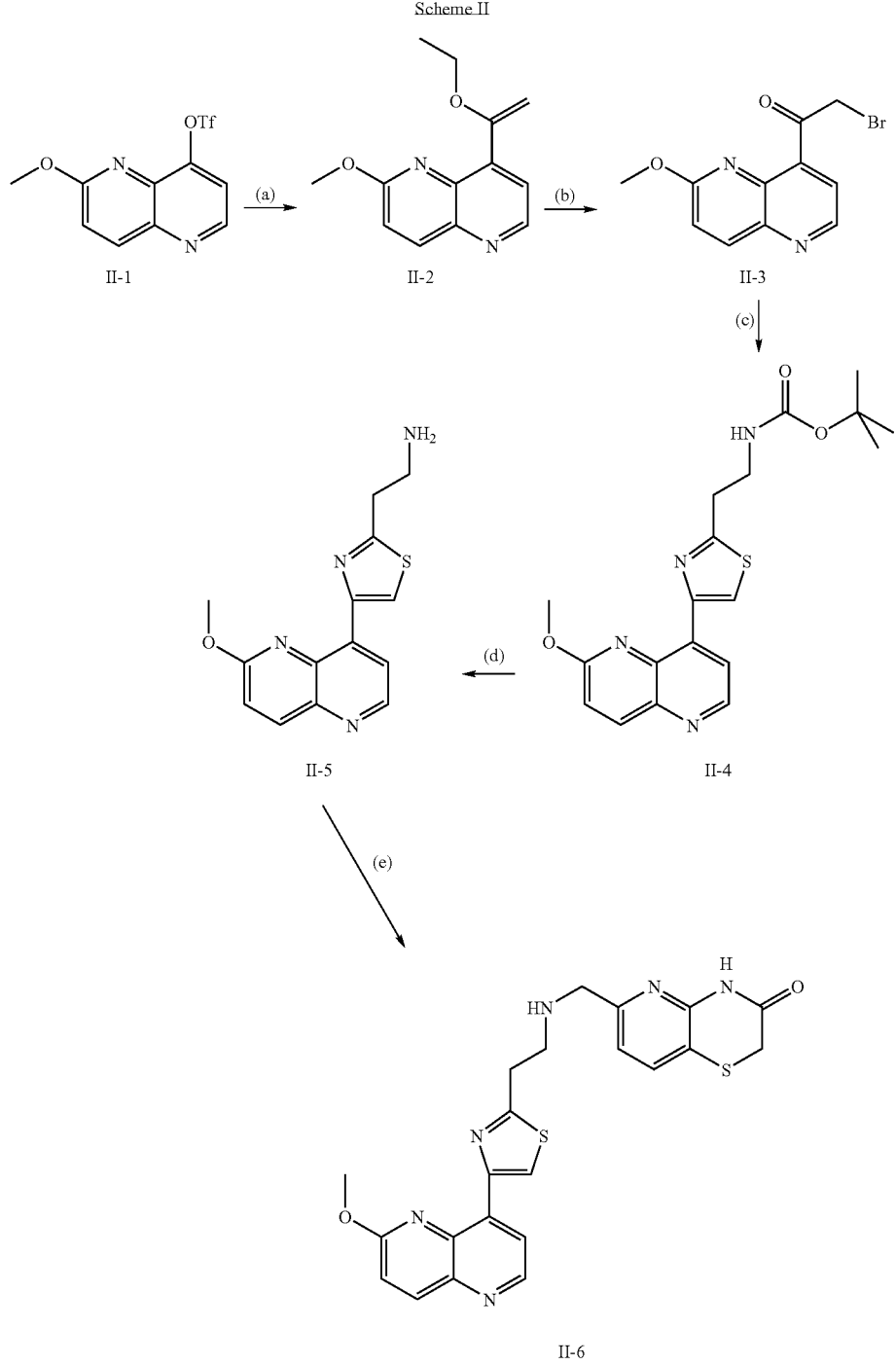

Reagents and conditions:
(a) butyl vinyl ether, palladium (II) acetate, 1,3-bis(diphenylphosphino)propane, Et$_3$N, DMF; (b) N-bromosuccinimide, THF, H$_2$O;
(c) 1,1-dimethylethyl (3-amino-3-thioxopropyl)carbamate, ethanol, NaHCO$_3$; (d) trifluoroacetic acid; (e) methanol/dimethylformamide/
acetic acid, 3-oxo-3,4-dihydro-2H-pyrido[3,2-b][1,4]thiazine-6-carbaldehyde, sodium cyanoborohydride.

Triflate (II-1) is reacted under Heck coupling conditions to afford II-2, (for a review, see Beletskaya, Irina P.; Cheprakov, Andrei V., Chemical Reviews (Washington, D. C.) (2000), 100(8), 3009–3066). Reaction of vinyl ether II-2 with N-bromosuccinimide under aqueous conditions gives bromomethyl ketone II-3 (see for example, Dhar, T. G. et al, Journal of Medicinal Chemistry (2002), 45(11), 2127–2130). This is reacted with 1,1-dimethylethyl (3-amino-3-thioxopropyl)carbamate according to standard thiazole condensation conditions to give II-4 (see for example Ikemoto, N. et al, Tetrahedron (2003), 59(8), 1317–1325). The tert-butyloxycarbonyl protecting group is removed under standard conditions (trifluoroacetic acid, followed by workup with aqueous sodium bicarbonate solution) to give II-5. The amine is then reacted with the aldehyde in a reductive alkylation reaction using sodium cyanoborohydride to give II-6.

The pharmaceutical compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or a pharmaceutically acceptable salt or in viva hydrolysable ester thereof is administered in the abovementioned dosage range.

The compound of formula (I) may be the sole therapeutic agent in the compositions of the invention or a combination with other antibiotics or with a β-lactamase inhibitor may be employed.

Compounds of formula (I) are active against a wide range of organisms including both Gram-negative and Gram-positive organisms.

The following examples illustrate the preparation of certain compounds of formula (I) and the activity of certain compounds of formula (I) against various bacterial organisms.

BIOLOGICAL ACTIVITY

Antimicrobial Activity Assay

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically". The compounds were tested in serial two-fold dilutions ranging from 0.016 to 64 mcg/mL. Compounds were evaluated against a panel of Gram-(+) organisms, including *Staphylococcus aureus* WCUH29, *Streptococcus pneumoniae* 1629, *Enterococcus faecalis* 2, and In addition, compounds were evaluated against a panel of Gram-(−) strains including, *Haemophilus influenzae* NEMC1, *E. coli* 7623 and AcrABEFD The minimum inhibitory concentration (MIC) was determined as the lowest concentration of compound that inhibited visible growth. A mirror reader was used to assist in determining the MIC endpoint.

One skilled in the art would consider any compound with a MIC of less than 64 µg/mL to be a potential lead compound. Preferably, the compounds used in the antimicrobial assays of the present invention have a MIC value of less than 16 µg/mL.

EXPERIMENTAL

General

Proton nuclear magnetic resonance ($^1$H NMR) spectra were recorded at 300 MHz, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. CDCl$_3$ is deuteriochloroform, DMSO-d$_6$ is hexadeuteriodimethylsulfoxide, and CD$_3$OD is tetradeuteriomethanol. Mass spectra were obtained using electrospray (ES) ionization techniques. Elemental analyses were performed by Quantitative Technologies Inc., Whitehouse, N.J. Melting points were obtained on a Thomas-Hoover melting point apparatus and are uncorrected. All temperatures are reported in degrees Celsius. E. Merck Silica Gel 60 F-254 thin layer plates were used for thin layer chromatography. Flash chromatography was carried out on E. Merck Kieselgel 60 (230–400 mesh) silica gel. Analytical HPLC was performed on Beckman chromatography systems. Preparative HPLC was performed using Gilson chromatography systems. ODS refers to an octadecylsilyl derivatized silica gel chromatographic support. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

Preparation 1

Preparation of 1,1,1-Trifluoromethanesulfonic acid 6-methoxy-[1,5]naphthyridin-4-yl ester a) 4-Hydroxy-6-methoxy-[1,5]-naphthyridine 5-Amino-2-methoxypyridine (55.0 g, 0.44 mole) in methanol (1000 mL) with methyl propiolate (40 mL, 0.44 mole) was stirred for 48 hours, then evaporated and the product purified by chromatography on silica gel (dichloromethane) followed by recrystallization from dichloromethane-hexane (44.6 g, 48%). The unsaturated ester (10.5 g, 0.05 mole) in warm Dowtherm A (50 mL) was added over 3 minutes to refluxing Dowtherm A, and after a further 20 minutes at reflux the mixture was cooled and poured into diethyl ether. The precipitate was filtered to give a solid (6.26 g, 70%).

b) 1,1,1-Trifluoromethanesulfonic acid 6-methoxy-[1,5]naphthyridin-4-yl ester

4-Hydroxy-6-methoxy-[1,5]naphthyridine (10 g, 0.057 mole) in dichloromethane (200 mL) containing 2,6-lutidine (9.94 mL, 0.086 mole) and 4-dimethylaminopyridine (0.07 g, 0.0057 mole) was cooled in ice and treated with trifluoromethanesulfonic anhydride (10.5 mL, 0.063 mole). After stirring for 2.5 hours the mixture was washed with saturated ammonium chloride solution, dried, evaporated and purified on silica gel (dichloromethane) to give a light yellow solid (13.2 g, 75%). LC-MS (ES) m/e 309 (M+H)$^+$.

Preparation 2

Preparation of 3-oxo-3,4-dihydro-2H-benzo[1,4]thiazine-6-sulfonyl chloride

Powdered 4H benzo[1,4]thiazin-3-one (7.0g) was added cautiously, portionwise (over 20 minutes), to chlorosulfonic acid (15 mL), cooled in ice. After 1 hour, the blue solution was allowed to warm to room temperature and it was heated at 45° C. for 2 hours, cooled and poured into ice. The solid was collected, washed with water, and hexane, and dried in vacuo, to give a white solid (7.0 g): LC-MS (ES) m/e 263 (M)$^+$.

EXAMPLE 1

Preparation of 3-Oxo-3,4-dihydro-2H-benzo[1,4]thiazine-6-sulfonic acid {3-[4-(6-methoxy-[1,5]naphthyridin-4-yl)-[1,2,3]triazol-1-yl]-propyl}amide a) 2-Methoxy-8-trimethylsilanylethynyl-[1,5]naphthyridine 1,1,1-Trifluoro-methanesulfonic acid 6-methoxy-[1,5]naphthyridin-4-yl ester (10 g, 32 mmol) was partially dissolved in triethylamine (80 mL) and dichloromethane was added in small portions until solid was completely dissolved. The resulting solution was degassed and purged with nitrogen, then treated with (trimethylsilyl)acetylene (5 mL, 36 mmole), bis-(triphenylphosphine)palladium (II) chloride (456 mg, 0.65 mmole), and copper (I) iodide (125 mg, 0.65 mmol) at room temperature overnight. Reaction mixture was concentrated to near dryness, then redissolved in ethyl acetate and washed with water and brine. Insoluble material was filtered off and aqueous layer was dried over sodium sulfate, filtered and concentrated. The resulting brown thick oil was used without further purification.

LC-MS (ES) m/e 257 (M+H)+.

b) 8-Ethynyl-2-methoxy-[1,5]naphthyridine

A solution of 2-Methoxy-8-trimethylsilanylethynyl-[1,5] naphthyridine in methanol (80 mL) was treated with potassium carbonate (4.49 g, 32 mmole) and stirred 1.5 hrs. The reaction mixture was concentrated to dryness, redissolved in ethyl acetate, and partitioned with brine. The biphasic mixture was filtered to facilitate separation. Organic layer was dried over sodium sulfate, filtered, concentrated and chromatographed in 1:1 ethyl acetate:hexane to give the product as a cream colored solid. δH (CDCl$_3$, 400 MHz), 8.73 (d, J=4Hz, 1 H), 8.20 (d, J=9 Hz, 1 H), 7.68 (d, J=4 Hz, 1H), 7.16 (d, J=9 Hz, 1 H), 4.15 (s, 3H), 3.67 (s, 1H).

LC-MS (ES) m/e 185 (M+H)+.

c) 2-{3-[4-(6-Methoxy-[1,5]naphthyridin-4-yl)-[1,2,3]triazol-1-yl]-propyl}-isoindole-1,3-dione A mixture of 8-ethynyl-2-methoxy-[1,5]naphthyridine (184 mg, 1.0 mmole) and 2-(3-azido-propyl)-isoindole-1, 3-dione (230 mg, 1.0 mmole) were refluxed in toluene (5 mL) for 12 hours. Upon cooling the product precipitated. The mixture was diluted with ether (5 mL) filtered, and the solid product was washed with ether and dried to give 190 mg (46%) of 2-{3-[4-(6-Methoxy-[1,5]naphthyridin-4-yl)-[1,2,3]triazol-1-yl]-propyl}-isoindole-1,3-dione as a grey solid as single regioisomer.

$^1$H NMR (400 MHz, CDCl$_3$): 9.10 (s, 1H); 8.85 (d, J=4.7Hz, 1H); 8.52 (d, J=4.7 Hz, 1H); 8.27 (d, J=9.1 Hz, 1H); 7.79 (m, 2H); 7.67 (m, 2H); 7.21 (d, J=9.1 Hz, 1H); 4.57 (t, J=6.6 Hz, 2H); 4.22 (s, 3H); 3.83 (t, J=6.3 Hz, 2H); 2.47 (m, 2H).

d) 3-Oxo-3,4-dihydro-2H-benzo[1,4]thiazine-6-sulfonic acid {3-[4-(6-methoxy-[1,5]naphthyridin-4-yl)-[1,2,3]triazol-1-yl]-propyl}amide To a suspension of 2-{3-[4-(6-Methoxy-[1,5]naphthyridin-4-yl)-[1,2,3]triazol-1-yl]-propyl)-isoindole-1,3-dione (180 mg, 0.43 mmole) in ethanol (3 mL) was added hydrazine hydrate (23 μL, 0.48 mmole) and the mixture was brought to reflux for 3 hours. After cooling 0.1 mL of 6N aqueous HCl was added to dissolve the product. The mixture was filtered and the filtrate was concentrated to dryness to afford the crude amine hydrochloride (85 mg). This material was suspended in chloroform (3 mL) and treated with triethylamine (0.18 mL, 1.3 mmole), followed by 3-oxo-3, 4-dihydro-2H benzo[1,4]thiazine-6-sulfonyl chloride (100 mg, 0.4 mmole). After stirring 1 hour the mixture was diluted with chloroform, washed with saturated aqueous NaHCO$_3$, dried (MgSO$_4$), and chromatographed on silica (0–5% methanovchloroform) to provide the title compound as an off-white solid (60 mg, 27%). $^1$H NMR (400 MHz, DMSO-d6): 10.83 (br s, 1 H); 9.05 (s, 1 H); 8.84 (d, 1H); 8.37 (d, 1H); 8.29 (d, 1H); 7.85 (m, 1H); 7.46 (d, 1H); 7.24–7.42 (m, 3H); 4.60 (m, 2H); 4.17 (s, 3H); 3.53 (s, 2H); 2.80 (m, 2H); 2.14 (m, 2H). LC-MS (ES) m/e 512 (M+H)$^+$.

EXAMPLE 2

Preparation of 6-{[(2-{4-[6-(methoxy)-1,5-naphthyridin-4-yl]-1,3-thiazol-2-yl}ethyl)amino]methyl}-2H-pyrido[3,2-b][1,4]thiazin-3(4H)-one dihydrochloride (a) 8-(1-Butoxy-vinyl)-7-chloro-2-methoxy-[1,5]naphthyridine The triflate (1b) (8.8 g) in DMF (80 mL) with triethylamine (7.2 mL) butyl vinyl ether (19.3 mL), palladium (II) acetate (0.584 g) and 1,3-bis(diphenylphosphino)propane (1.06 g) was heated at 65–70° C. for 30 hours then evaporated, azeotroped with toluene, and chromatographed on silica gel (dichloromethane-hexane) to give a solid (3.7 g).
MS (ES) m/z293/295 (M+H)$^+$.

(b) 2-Bromo-1-(3-chloro-6-methoxy-[1,5]naphthyridin-4-yl)-ethanone

The vinyl ether (a) (6.51 g) was dissolved in THF (100 mL), and water (9 mL) and treated with N-bromosuccinimide (6.51 g) for 5 hour, then evaporated and chromatographed on silica gel (dichloromethane-hexane) to give the bromomethylketone as a solid (8.9 g).
MS (ES) m/z3151317 (M+H)$^+$.

(c) 1,1-dimethylethyl (2-(4-[6-(methoxy)-1,5-naphthyridin-4-yl]-1,3-thiazol-2-yl}ethyl)carbamate A mixture of bromomethylketone (b) (2.07 g, 9 mmol), 1,1-dimethylethyl (3-amino-3-thioxopropyl)carbamate (1.84 g, 9 mmol) and sodium bicarbonate (0.76 g, 9 mmol) in ethanol (120 mL) was heated to reflux for 1 hour under argon. The mixture was evaporated and the residue partitioned between ethyl acetate and aqueous sodium bicarbonate solution. The organic extract was washed with brine, dried and evaporated. The residue was chromatographed on silica eluting with a gradient of 0–50% ethyl acetate in dichloromethane affording a yellow solid (0.93 g, 26%).
MS (ES) m/z 387 (M+H)$^+$.

(d) (2-(4-[6-(methyloxy)-1,5-naphthyridin-4-yl]-1,3-thiazol-2-yl)ethyl)amine

The carbamate (c) (0.93 g, 2.4 mmol) was dissolved in trifluoroacetic acid (40 mL). After 1 hour the mixture was evaporated and the residue partitioned between ethyl acetate and aqueous sodium bicarbonate solution. The organic extract was washed with brine, dried and evaporated affording a solid (2.17 g, 90%).
MS (ES) m/z 287 (M+H)$^+$.

(e) Title Compound

A mixture of amine (d) (0.14 g, 0.5 mmol) and 3-oxo-3, 4-dihydro-2H-pyrido[3,2-b][1,4]thiazine-6-carbaldehyde (0.1 g, 0.5 mmol) in methanol/dimethylformamide/acetic acid (6 mL/6 mL/0.6 mL) was heated at 80° C. for 2 hours then allowed to cool to room temperature. Sodium cyanoborohydride (63 mg, 1 mmol) was added and the mixture stirred overnight at room temperature. The mixture was partitioned between chloroform and aqueous sodium bicarbonate solution. The organic phase was separated, dried and evaporated. The residue was chromatographed on silica eluting with a gradient of 0–10% methanol in ethyl acetate affording a solid (31 mg, 14%).
$^1$H NMR δH (400 MHz, CDCl$_3$) δ 9.02 (1H, s), 8.85 (1H, d), 8.45 (1H, d), 8.28 (1H, d), 7.57 (1H, d), 7.20 (1H, d), 7.00 (1H, d), 4.12 (3H, s), 3.90 (2H, s), 3.45 (2H, s), 3.32 (2H, m), 3.18 (2H, m),
MS (ES) m/z465 (M+H)$^+$.

What is claimed is:

1. A compound according to formula (I)

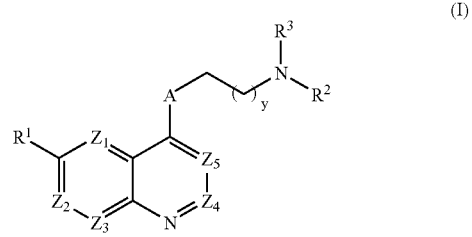

one of $Z_1$, $Z_2$, $Z_3$, $Z_4$ and $Z_5$ is N, one is $CR^{1a}$ and the remainder are CH, or one or two of $Z_1$, $Z_2$, $Z_3$, $Z_4$ and $Z_5$ are independently $CR^{1a}$ and the remainder are CH;

$R^1$ and $R^{1a}$ are independently hydrogen; hydroxy; ($C_{1-6}$) alkoxy unsubstituted or substituted by ($C_{1-6}$)alkoxy, amino, piperidyl, guanidino or amidino any of which is optionally N-substituted by one or two ($C_{1-6}$)alkyl, acyl or ($C_{1-6}$)alkylsulphonyl groups, CONH$_2$, hydroxy, ($C_{1-6}$)alkylthio, heterocyclylthio, heterocyclyloxy, arylthio, aryloxy, acylthio, acyloxy or ($C_{1-6}$)alkylsulphonyloxy; ($C_{1-6}$)alkoxy-substituted($C_{1-6}$)alkyl; halogen; ($C_{1-6}$)alkyl; ($C_{1-6}$)alkylthio; trifluoromethyl; trifluoromethoxy; nitro; cyano; azido; acyl; acyloxy; acylthio; ($C_{1-6}$)alkylsulphonyl; ($C_{1-6}$)alkylsulphoxide; arylsulphonyl; arylsulphoxide or an amino, piperidyl, guanidino or amidino group optionally N-substituted by one or two ($C_{1-6}$)alkyl, acyl or ($C_{1-6}$)alkylsulphonyl groups;

provided that when $Z_1$, $Z_2$, $Z_3$, $Z_4$ and $Z_5$ are $CR^{1a}$ or CH, then $R^1$ is not hydrogen;

A is a substituted or unsubstituted 5 membered aromatic heterocyclic ring of formula (C):

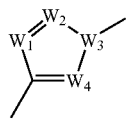

wherein:

$W_1$ and $W_2$ are each independently selected from N, O, S, and $CR^8$;

$W_3$ is N or C;

$W_4$ is N, O, S, or $CR^8$;

each $R^8$ is independently selected from hydrogen; hydroxy; halogen; trifluoromethyl; trifluoromethoxy; cyano; nitro; azido; acyl; acyloxy; acylthio; amino, mono- and di-$(C_{1-6})$alkylamino; and substituted and unsubstituted $(C_{1-6})$alkoxy, $(C_{1-6})$alkyl, $(C_{3-7})$cycloalkyl, aminocarbonyl, $(C_{1-6})$alkylthio, $(C_{1-6})$alkylsulphonyl, and $(C_{1-6})$alkylsulphoxide;

$R^2$ is hydrogen, or $(C_{1-6})$alkyl or $(C_{2-6})$alkenyl optionally substituted with 1 to 3 groups selected from:

amino optionally substituted by one or two $(C_{1-4})$alkyl groups; carboxy; $(C_{1-4})$alkoxycarbonyl; $(C_{1-4})$alkylcarbonyl; $(C_{2-4})$alkenyloxycarbonyl; $(C_{2-4})$alkenylcarbonyl; aminocarbonyl wherein the amino group is optionally substituted by hydroxy, $(C_{1-4})$alkyl, hydroxy$(C_{1-4})$alkyl, aminocarbonyl $(C_{1-4})$alkyl, $(C_{2-4})$alkenyl, $(C_{1-4})$alkylsulphonyl, trifluoromethylsulphonyl, $(C_{2-4})$alkenylsulphonyl, $(C_{1-4})$alkoxycarbonyl, $(C_{1-4})$alkylcarbonyl, $(C_{2-4})$alkenyloxycarbonyl or $(C_{2-4})$alkenylcarbonyl; cyano; tetrazolyl; 3-hydroxy-3-cycloalkene-1,2-dione-4-yl; 2,4-thiazolidinedione-5-yl; tetrazol-5-ylaminocarbonyl; 5-oxo-1,2,4-oxadiazol-3-yl; halogen; $(C_{1-4})$alkylthio; trifluoromethyl; hydroxy optionally substituted by $(C_{1-4})$alkyl, $(C_{2-4})$alkenyl, $(C_{1-4})$alkoxycarbonyl, $(C_{1-4})$alkylcarbonyl, $(C_{2-4})$alkenyloxycarbonyl, $(C_{2-4})$alkenylcarbonyl; oxo; $(C_{1-4})$alkylsulphonyl; $(C_{2-4})$alkenylsulphonyl; or $(C_{1-4})$aminosulphonyl wherein the amino group is optionally substituted by $(C_{1-4})$alkyl or $(C_{2-4})$alkenyl;

$R^3$ is a group —U—$R^4$ where

U is selected from $CH_2$, C=O, and $SO_2$ and $R^4$ is a substituted or unsubstituted bicyclic carbocyclic or heterocyclic ring system (A):

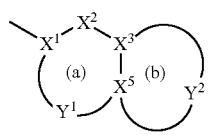

containing up to four heteroatoms in each ring in which ring (a) is aromatic and ring (b) is aromatic or non-aromatic;

$X^1$ is C;

$X^2$ is N or $CR^5$;

$X^3$ and $X^5$ are C;

$Y^1$ is a 1 to 2 atom linker group, each atom of which is independently selected from N and $CR^5$;

$Y^2$ is a 2 to 6 atom linker group, each atom of $Y^2$ being independently selected from N, $NR^7$, O, $S(O)x$, CO, $CR^5$ and $CR^5R^6$;

each of $R^5$ and $R^6$ is independently selected from: hydrogen; $(C_{1-4})$alkylthio; halo; carboxy$(C_{1-4})$alkyl; halo $(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy$(C_{1-4})$alkyl; mercapto $(C_{1-4})$alkyl; $(C_{1-4})$alkoxy; nitro; cyano; carboxy; amino or wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl; or $(C_{2-6})$alkenyl; $(C_{1-4})$alkylsulphonyl; $(C_{2-4})$alkenylsulphonyl; or aminosulphonyl wherein the amino group is optionally mono- or di-substituted by $(C_{1-4})$alkyl or $(C_{2-4})$alkenyl; aryl; aryl$(C_{1-4})$alkyl; or aryl$(C_{1-4})$alkoxy;

each $R^7$ is independently hydrogen; trifluoromethyl; $(C_{1-4})$alkyl unsubstituted or substituted by hydroxy, $(C_{1-6})$alkoxy, $(C_{1-6})$alkylthio, halo or trifluoromethyl; $(C_{2-4})$alkenyl; aryl; aryl $(C_{1-4})$alkyl; arylcarbonyl; heteroarylcarbonyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl; and x is 0, 1, or 2;

y is 1, or 2; or a pharmaceutically acceptable salt thereof.

2. A compound according to claim 1 wherein $Z_5$ is CH or N, $Z_3$ is CH or CF and $Z_1$, $Z_2$ and $Z_4$ are each CH, or $Z_1$ is N, $Z_3$ is CH or CF and $Z_2$, $Z_4$ and $Z_5$ are each CH.

3. A compound according to claim 1 wherein $R^1$ is methoxy and $R^{1a}$ is H or when $Z_3$ is $CR^{1a}$ it may be C—F.

4. A compound according to claim 1 wherein heterocyclic ring (C) is substituted or unsubstituted pyrrole, thiophene, furan, thiazole or triazole.

5. A compound according to claim 1 wherein $R^2$ is hydrogen or unsubstituted or substituted $(C_{1-6})$alkyl.

6. A compound according to claim 1 wherein in the heterocyclic ring (A) $Y^2$ has 3–5 atoms including $NR^7$, O or S bonded to $X^5$ and NHCO bonded via N to $X^3$, or O or NH bonded to $X^3$.

7. A compound according to claim 1 wherein $R^4$ is selected from:

4H-benzo[1,4]thiazin-3-one-6-yl,
4H-pyrido[3,2-b][1,4]thiazin-3-one-6-yl,
4H-pyrido[3,2-b][1,4]oxazin-3-one-6-yl,
1,2,3,4-tetrahydro-[1,8]naphthyridine-7-yl,
1H-pyrido[3,2-b][1,4]thiazin-2-one-7-yl,
4H-benzo[1,4]oxazin-3-one-6-yl, and
2,3-dihydro-[1,4]dioxino[2,3-c]-pyridin-7-yl, and
6-fluoro-2,3-dihydrobenzo[1,4]dioxine-7-yl.

8. A compound according to claim 1 which is 3-Oxo-3,4-dihydro-2H-benzo[1,4]thiazine-6-sulfonic acid {3-[4-(6-methoxy-[1,5]naphthyridin-4-yl)-[1,2,3]triazol-1-yl]-propyl}amide or 6-{[(2-{4-[6-(methoxy)-1,5-naphthyridin-4-yl]-1,3-thiazol-2-yl}ethyl)amino]methyl}-2H-pyrido[3,2-b][1,4]thiazin-3(4H)-one dihydrochloride
or a pharmaceutically acceptable salt thereof.

9. A method of treatment of bacterial infections in mammals which comprises the administration to a mammal in need thereof an effective amount of a compound according to claim 1.

10. A pharmaceutical composition comprising a compound according to claim 1 and a pharmaceutically acceptable carrier for use in the treatment of bacterial infections in mammals.

11. A pharmaceutical composition comprising a compound according to claim 1, and a pharmaceutically acceptable carrier.

* * * * *